US009778222B2

(12) United States Patent
Matsumoto et al.

(10) Patent No.: US 9,778,222 B2
(45) Date of Patent: Oct. 3, 2017

(54) CAPILLARY UNIT FOR ELECTROPHORESIS AND ELECTROPHORESIS DEVICE COMPRISING THE CAPILLARY UNIT

(71) Applicant: SHIMADZU CORPORATION, Kyoto-shi, Kyoto (JP)

(72) Inventors: Hiroyuki Matsumoto, Kyoto (JP); Shin Nakamura, Kyoto (KR); Toru Kaji, Kyoto (JP); Tomonori Nozawa, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 51 days.

(21) Appl. No.: 14/769,181

(22) PCT Filed: Feb. 25, 2013

(86) PCT No.: PCT/JP2013/054717
§ 371 (c)(1),
(2) Date: Aug. 20, 2015

(87) PCT Pub. No.: WO2014/128956
PCT Pub. Date: Aug. 28, 2014

(65) Prior Publication Data
US 2015/0377829 A1 Dec. 31, 2015

(51) Int. Cl.
*G01N 27/447* (2006.01)
*B01L 3/00* (2006.01)

(52) U.S. Cl.
CPC .. *G01N 27/44743* (2013.01); *B01L 3/502715* (2013.01); *G01N 27/44704* (2013.01);
(Continued)

(58) Field of Classification Search
CPC .... B81B 1/00–1/004; G01N 27/44791; G01N 27/453; G01N 27/44739; G01N 30/16; G01N 30/167
See application file for complete search history.

(56) References Cited

U.S. PATENT DOCUMENTS 6,635,164 B1  10/2003  Anazawa et al.
7,655,125 B2   2/2010  Nakamura et al.
(Continued)

FOREIGN PATENT DOCUMENTS

JP    11-248678 A    9/1999
JP   2001-124736 A   5/2001
(Continued)

OTHER PUBLICATIONS

JPO computer-generated Englsih langauge translation of JP 2001-124736 A. Downloaded Jan. 9, 2017.*
(Continued)

*Primary Examiner* — Alexander Noguerola
(74) *Attorney, Agent, or Firm* — Westerman, Hattori, Daniels & Adrian, LLP

(57) ABSTRACT

A capillary unit includes a reservoir capable of retaining a liquid. A capillary having a linear shape has one end secured on a bottom-end portion of the reservoir. The capillary extends from the bottom-end portion in a direction away from an opening of the reservoir. A nozzle connector is provided between a bottom of the reservoir and the one end of the capillary, and provides liquid-tight removable connection with a nozzle for injecting the liquid into the capillary from a portion adjacent to the reservoir.

9 Claims, 9 Drawing Sheets

(52) U.S. Cl.
 CPC ......... *G01N 27/44721* (2013.01); *G01N 27/44756* (2013.01); *G01N 27/44791* (2013.01); *B01L 2200/06* (2013.01)

(56) References Cited

U.S. PATENT DOCUMENTS

| | | |
|---|---|---|
| 2002/0179446 A1 | 12/2002 | Kasai et al. |
| 2009/0183634 A1* | 7/2009 | Zeeuw ............... G01N 30/16 96/106 |
| 2010/0170799 A1 | 7/2010 | Amirkhanian et al. |

FOREIGN PATENT DOCUMENTS

| | | |
|---|---|---|
| JP | 2001-281221 A | 10/2001 |
| JP | 2004-251680 A | 9/2004 |
| JP | 2006-201188 A | 8/2006 |

OTHER PUBLICATIONS

International Search Report dated Apr. 9, 2013, issued in counterpart Application No. PCT/JP20131054717 (2 pages).

\* cited by examiner

CAPILLARY UNIT FOR ELECTROPHORESIS AND ELECTROPHORESIS DEVICE COMPRISING THE CAPILLARY UNIT

TECHNICAL FIELD

The present invention relates to a capillary unit including a capillary that is used as a migration channel for electrophoretic analysis, and to an electrophoresis device having the capillary unit.

BACKGROUND ART

Electrophoresis devices have conventionally been used for analyzing a trace of protein, nucleic acid, or other material. Typical electrophoresis devices include a microchip electrophoresis device and a capillary electrophoresis device.

A microchip electrophoresis device uses a microchip having a fine flow channel in a substrate, and a well or a reservoir is formed at each end of the flow channel. Typically, the microchip is placed horizontally, and is regulated to maintain a constant temperature. The well or reservoir at each end of the flow channel is accessed by an autosampler a polymer (separation medium) feeding mechanism, an inlet nozzle, an electrode, and the like thereby to feed the separation medium, and introduce a sample, into the capillary, to feed buffer solution to the reservoir, and to perform electrophoretic analysis (see, e.g., Patent Document 1).

A capillary electrophoresis device uses a capillary as the migration channel. Typically, the capillary is placed horizontally, and a member having a reservoir is secured at each end of the capillary. Through that member, the separation medium is fed into the capillary, a sample is introduced, and electrophoretic analysis is performed.

PRIOR ART DOCUMENTS

Patent Documents

Patent Document 1: U.S. Pat. No. 7,655,125 B2
Patent Document 2: US Patent Application Publication No. 2010/0170799

SUMMARY OF THE INVENTION

Problems to be Solved by the Invention

The microchip electrophoresis device and the capillary electrophoresis device described above each perform an operation in such a way that a separation medium is fed into the horizontally-placed flow channel from one end of that flow channel, after which excess separation medium remaining in the reservoir provided at the end of the flow channel is suctioned and removed by an inlet nozzle. Also, after a sample has been introduced to the flow channel, an operation is performed in such a way that excess sample remaining in the sample reservoir provided at the end of the flow channel is suctioned and removed by the inlet nozzle.

To eliminate the need for the suction and removal operation described above, some electrophoresis devices are configured in such a way that the capillary is bent at a certain point of the capillary, and the portion on the anode-end side is placed horizontally, whose anode end has an anode reservoir having a separation medium feeding mechanism and the like secured thereon, while the portion on the cathode-end side is placed vertically downward, whose cathode end is left open to allow the cathode end of the capillary to directly access a sample holder that holds the sample. The cathode end of the capillary being capable of a direct access to the sample in such electrophoresis device eliminates the need for an autosampler that introduces the sample to the capillary.

Bending the capillary, however, requires a certain length of the capillary, and thus, imposes a limitation on reduction in the length of the capillary when seeking to accelerate electrophoresis. Moreover, the migration distance in an inner portion will differ from that in an outer portion of the bend section. This difference causes a broad bandwidth at the detection peak, and decreases separation performance. The effects of the difference in the migration distance at the bend section of the capillary can be reduced by increasing the capillary length, whereas acceleration of electrophoresis cannot be achieved. Furthermore, installing the capillary having a bend section at a certain point of the capillary in the device is not an easy task, and may thus present a problem such as breakage of the capillary.

An electrophoresis device is also proposed which includes a cartridge having a reservoir that has preliminarily been filled with a separation medium, a capillary, and electrodes that are integrated with one another, wherein the cartridge is placed so that the capillary is in a vertical position to allow the lower end of the capillary of the cartridge to directly access the sample and the buffer solution (see Patent Document 2). Such electrophoresis device has the capillary of the cartridge preliminarily filled with the separation medium, and allows the lower end of the capillary to directly access the sample to introduce the sample. This configuration eliminates the need for the suction and removal operation of excess separation medium and of excess sample. In addition, a linear shape and the short length of the capillary of the cartridge can accelerate electrophoresis. However, the preliminary filling process of the capillary of the cartridge with the separation medium causes high production cost of the cartridge, and in addition, does not permit replacement of the separation medium in the capillary, thereby limiting the number of use cycles. This makes the cartridge a costly disposable.

An object of the present invention is, thus, to achieve accurate and easy feeding of a separation medium to the migration channel, and accurate and easy formation of a sample plug, and also to provide acceleration of electrophoresis by reducing the length of the capillary.

Solutions to the Problems

A capillary unit according to the present invention includes a reservoir formed of a concave portion capable of retaining a liquid, a capillary having a linear shape and extending in a direction away from an opening of the reservoir, one end of the capillary being secured on a bottom-end portion of the reservoir, and a nozzle connector provided between a bottom of the reservoir and the one end of the capillary, the nozzle connector being configured to provide liquid-tight removable connection with a nozzle for injecting a liquid into the capillary from the reservoir.

An electrophoresis device according to the present invention includes a capillary-unit placement unit configured to place the capillary unit of the present invention so that the capillary is in a vertical position a separation medium feeding mechanism having a nozzle that discharges a separation medium from a tip, and configured to connect the nozzle to the nozzle connector of the capillary unit placed in the capillary-unit placement unit to feed the separation medium into the capillary, a buffer solution supply mechanism configured to supply a buffer solution to a reservoir of the capillary unit, a sample holder configured to hold a sample in the sample holder, having an open top to allow a lower end of the capillary to contact with the sample, and to be positioned below the capillary-unit placement unit when the lower end of the capillary comes into contact with the sample, a buffer reservoir configured to hold the buffer solution in the buffer reservoir, having an open top to allow the lower end of the capillary to contact with the buffer solution, and to be positioned below the capillary-unit placement unit when the lower end of the capillary comes into contact with the buffer solution, electrodes for applying a voltage across both ends of the capillary, and a detector configured to optically detect the sample that migrates in the capillary.

Effects of the Invention

A capillary unit of the present invention is configured in such a way that one end of the capillary having a linear shape is secured on a bottom-end portion of a reservoir formed of a concave portion capable of retaining a liquid, that the capillary extends in the direction away from an opening of the reservoir, and that a nozzle connector is provided between the bottom of the reservoir and the one end of the capillary, which nozzle connector provides liquid-tight removable connection with a nozzle for injecting the liquid into the capillary from a reservoir side. This simplifies the configuration of the capillary unit, and therefore permits low cost production and easy attachment to, and detachment from, the electrophoresis device. The linear shape of the capillary also permits a reduction in the capillary length to accelerate electrophoresis.

An electrophoresis device of the present invention includes a capillary-unit placement unit that places the capillary unit of the present invention so that the capillary is in a vertical position, feeds the separation medium into the capillary by injecting the separation medium from the upper-end side of the capillary using the nozzle with the lower end of the capillary open, and introduces the sample into the capillary by allowing the lower end of the capillary to directly access the sample or the buffer solution. This eliminates the need for the suction and removal operation of excess separation medium and of excess sample.

EMBODIMENTS OF THE INVENTION

Figure 1:
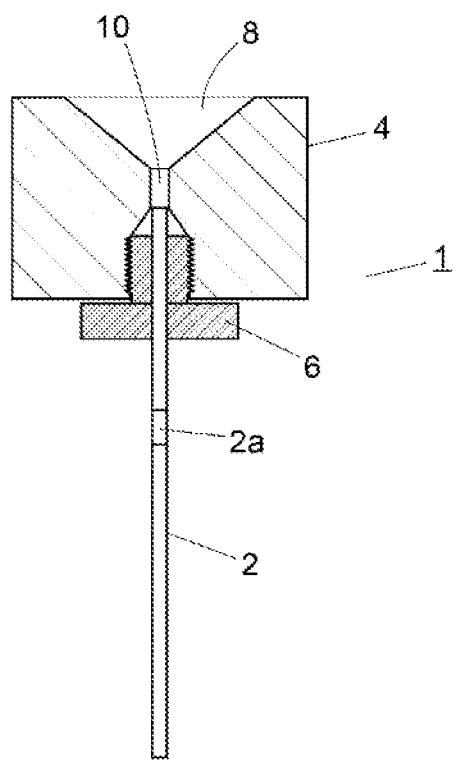
FIG. 1 is a partially cross-sectional view illustrating one embodiment of a capillary unit.

A capillary unit of the present invention may be provided with a plurality of capillaries and a plurality of reservoirs respectively associated with the capillaries and these reservoirs may be integrated with one another. Thus, a multi-capillary electrophoresis device can be achieved using the capillary unit of the present invention.

Moreover, the capillary unit of the present invention may be provided with a plurality of capillaries, and each capillary may be connected to a common reservoir respectively through a plurality of nozzle connectors. Thus, a multi-capillary electrophoresis device can be achieved using the capillary unit of the present invention.

It is preferable that an electrophoresis device of the present invention be configured in such a way that the capillary-unit placement unit includes a thermally conductive block that holds a portion other than the lower end of the capillary, and a heater that heats the block. This can provide temperature control of the capillary which is a migration channel, and thus, can stabilize separation performance.

In such a case, the heater is preferably a rubber heater attached over one entire surface of the block. Since the capillary-unit placement unit places the capillary in a vertical position, the capillary is vertically long, and thus, a temperature gradient is likely to be generated. Accordingly, attaching a rubber heater over the one entire surface of the block included in the capillary-unit placement unit to heat the entire surface of the block makes it less likely that a vertical temperature gradient will be generated, thus permitting the temperature control of the capillary to be more uniform.

According to a preferred aspect of an electrophoresis device of the present invention, the sample holder and the buffer reservoir are provided on a movable stage that is movable along a direction in a horizontal plane and a vertical direction, so that movement of the stage causes the lower end of the capillary to contact with the sample in the sample holder and the lower end of the capillary to contact with the buffer solution in the buffer reservoir.

An electrophoresis device of the present invention may include, as a control unit that controls the operation of the electrophoresis device, a control unit configured to introduce the sample into the capillary by applying a voltage across both ends of the capillary with the lower end of the capillary being in contact with the sample in the sample holder after feeding the separation medium into the capillary and then feeding the buffer solution to the reservoir of the capillary unit.

In addition, an electrophoresis device of the present invention may include, as a control unit that controls the operation of the electrophoresis device, a control unit configured to introduce the sample into the capillary by inserting the lower end of the capillary into the sample holder with the nozzle being connected to the nozzle connector and suctioning the separation medium in the capillary using the nozzle after the nozzle is connected to the nozzle connector of the capillary unit, and then the separation medium is fed into the capillary.

One embodiment of the capillary unit will be described below using FIG. 1. FIG. 1 is a partially cross-sectional view illustrating one embodiment of the capillary unit. This figure provides a front view of a capillary 2, and a cross-sectional view of the portions other than the capillary 2.

A capillary unit 1 includes the capillary 2 having a linear shape, and a reservoir block 4. The reservoir block 4 includes a reservoir 8 formed of a concave portion capable of retaining a liquid. The capillary 2 has one end secured on a bottom-end portion of the reservoir 8 of the reservoir block 4 by a ferrule 6 so as to extend in a direction away from an opening of the reservoir 8. The reservoir block 4 is made of for example, polybutylene terephthalate (PBT). The capillary 2 may be secured to the reservoir block 4 through adhesion by adhesive.

A part of the capillary 2 is formed as a detection position 2a, where a protective film covering the surface of the capillary 2 is removed, and thus, optical measurement, such as absorbance measurement or fluorescence measurement, of the inside of the capillary 2 can be made.

The reservoir block 4 includes a nozzle connector 10 that connects the bottom of the reservoir 8 to the one end of the capillary 2, and which provides liquid-tight connection with a nozzle for injecting the liquid into the capillary 2 from the reservoir 8 side.

Figure 2:
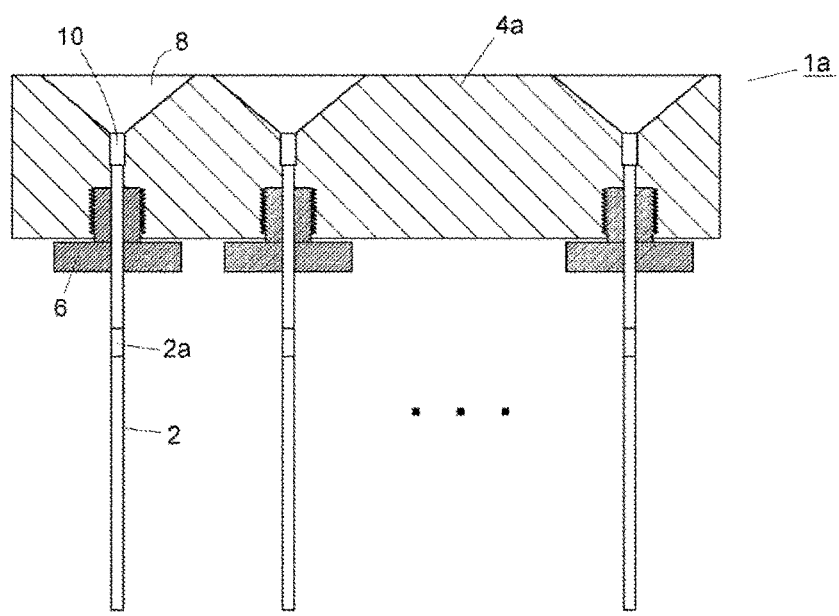
FIG. 2 is a partially cross-sectional view illustrating another embodiment of the capillary unit.

FIG. 2 is a partially cross-sectional view illustrating another embodiment of the capillary unit. This figure also provides a front view of the capillaries 2, and a cross-sectional view of the portions other than the capillaries 2.

A capillary unit 1a of this embodiment includes a plurality of capillaries 2 and a reservoir block 4a. The reservoir block 4a is provided with reservoirs 8 respectively associated with the capillaries 2, and one end of each of the capillaries 2 is secured to the reservoir block 4a in a bottom-end portion of the associated reservoir 8 by the ferrule 6.

A nozzle connector 10 is provided between the bottom of each of the reservoirs 8 and the one end of each of the capillaries 2. Each of the nozzle connectors 10 can provide liquid-tight removable connection with a nozzle for injecting the liquid. The capillaries 2 may be secured to the reservoir block 4a through adhesion by adhesive.

Figure 3:
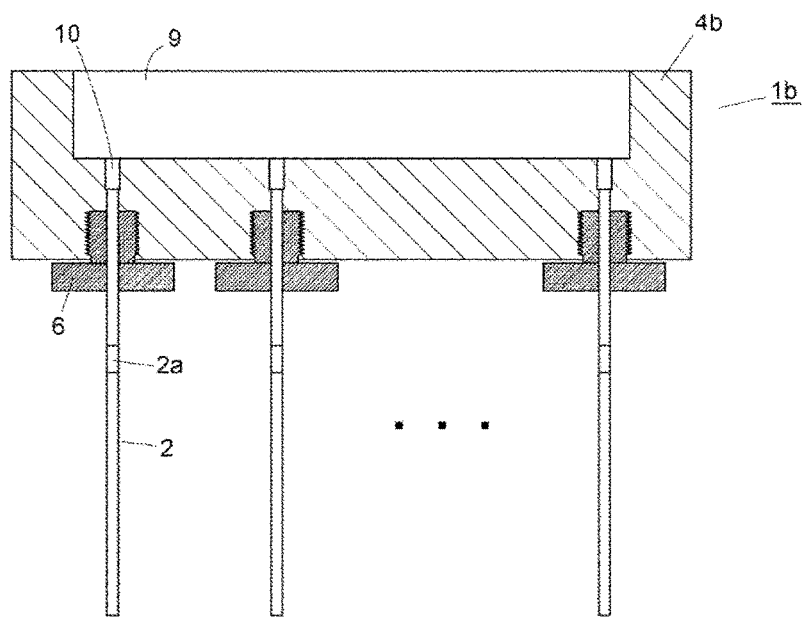
FIG. 3 is a partially cross-sectional' view illustrating still another embodiment of the capillary unit.

FIG. 3 is a partially cross-sectional view illustrating another embodiment of the capillary unit. This figure also provides a front view of the capillaries 2, and a cross-sectional view of the portions other than the capillaries 2.

A capillary unit 1b of this embodiment includes a plurality of capillaries 2 and a reservoir block 4b. The reservoir block 4b is provided with a reservoir 9 shared by all the capillaries 2. One end of each of the capillaries 2 is secured to the reservoir block 4b in a bottom-end portion of the common reservoir 9 by the ferrule 6.

A nozzle connector 10 is provided between the bottom of the reservoir 9 and the one end of each of the capillaries 2. Each of the nozzle connectors 10 can provide liquid-tight removable connection with a nozzle for injecting the liquid. The capillaries 2 may be secured to the reservoir block 4a through adhesion by adhesive.

Next, one embodiment of an electrophoresis device will be described using FIG. 4. Although this electrophoresis device employs the capillary unit 1 that has been described using FIG. 1, the capillary unit 1a described using FIG. 2 and the capillary unit 1b described using FIG. 3 may also be applied to an electrophoresis device.

A capillary-unit placement unit 12 that places the capillary unit 1 is provided. The capillary-unit placement unit 12 holds the capillary unit 1 so that the capillary 2 is in a vertical position. A lower-end portion of the capillary 2 extends downward beyond the capillary-unit placement unit 12, thus allowing the lower-end portion of the capillary 2 to directly access the inside of a sample tube 28 or of a buffer reservoir 30, which will be described below. The capillary-unit placement unit 12 is provided with a heater 13 and a temperature sensor 14, which control the temperature of the capillary 2 so as to remain at a constant value.

Figure 5:
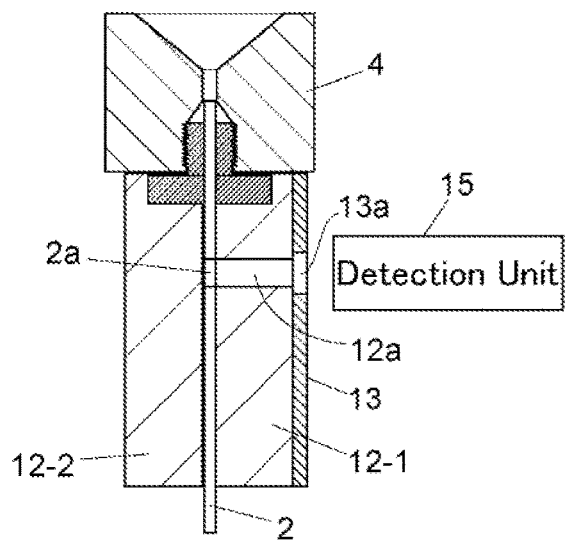
FIG. 5 is a cross-sectional view taken along line X-X of FIG. 4 illustrating a configuration of a capillary-unit placement unit of the same embodiment.

As shown in FIG. 5, the capillary-unit placement unit 12 includes two blocks 12-1 and 12-2 made of a highly thermally conductive metal, for example, aluminum and the like. These blocks 12-1 and 12-2 interpose and hold therebetween a portion of the ferrule 6 and the capillary 2 portion (except for the lower-end portion) of the capillary unit 12. A groove for placing the capillary unit 1 therein is formed in each of the inner surfaces facing each other of the two blocks. The heater 13, which is a rubber heater in sheet form, is attached over the entire surface of the block 12-1, which is one of the blocks included in the capillary-unit placement unit 12. The configuration that heats the entire surface of the block 12-1 by the heater 13 makes it less likely that a vertical temperature gradient will be generated in the block 12-1, which holds the capillary 2 in a vertical position, and in the capillary 2, thus permitting the temperature of the capillary 2 to be controlled uniformly in the vertical direction.

Holes 12a and 13a are respectively formed at predetermined positions of the block 12-1 and of the heater 13 to allow a detection unit 15 to optically detect a component of the sample migrating in the capillary 2 at the detection position 2a of the capillary 2. Examples of the detection unit 15 include one that has a detector and a light source arranged facing each other across the optical measurement portion 2a of the capillary 2, and which detects a change in absorbance in the capillary 2 based on the intensity of light transmitted through the capillary 2; and one that emits excitation light from a light source to the optical measurement portion 2a of the capillary 2, and which detects, by a detector, fluorescence from a component excited by the excitation light. A detection signal obtained in the detection unit 15 is received by an operation unit 20, which identifies a component of the sample and performs other operation. The operation unit 20 is implemented by, for example, a personal computer (PC) connected to the electrophoresis device, or a dedicated computer provided in the electrophoresis device.

An electrophoresis device using the capillary unit of FIG. 2 or FIG. 3 having the plurality of capillaries 2 may be provided with individual detection units 15 that respectively perform optical detection on the capillaries 2, or may be provided with a single detection unit 15 and a mechanism for horizontally moving the detection unit 15 to move the detection unit 15 to measurement positions sequentially for performing the optical detection on the respective capillaries 2, thereby to perform the optical detection sequentially.

In this embodiment, a separation medium feeding mechanism 22 and a buffer solution supply mechanism 24 are provided. The separation medium feeding mechanism 22 feeds polymer, which is the separation medium, into the capillary 2. The buffer solution supply mechanism 24 supplies the buffer solution to the reservoir 8 of the capillary unit 1.

The separation medium feeding mechanism 22 includes a nozzle 22a and a syringe pump 22b. The nozzle 22a and the syringe pump 22b are connected to each other via a tube. The nozzle 22a is movable horizontally and vertically, and can connect to the capillary 2 by inserting the tip into the nozzle connector 10 provided in the reservoir block 4 of the capillary unit 1.

The buffer solution supply mechanism 24 includes a nozzle 24a and a syringe pump 24b. The nozzle 24a and the syringe pump 24b are connected to each other via a tube. The nozzle 24a is movable horizontally and vertically.

A movable stage 26 is provided below the capillary-unit placement unit 12. Sample tubes 28 (sample holders) and a buffer reservoir 30 are placed, and a drain port 32 is provided, on the movable stage 26. The movable stage 26 is movable horizontally and vertically by means of a stage drive mechanism 27 to allow one of the sample tubes 28, the buffer reservoir 30, or the drain port 32 to access a lower-end portion of the capillary 2.

The sample tubes 28 each contain a sample therein. The buffer reservoir 30 contains a buffer solution therein. The drain port 32 is connected with a drain tube 34. Unnecessary liquid can be drained out through this drain port 32. The sample tubes 28 and the buffer reservoir 30 both have open tops to allow the lower end of the capillary 2 to access the sample in one of the sample tubes 28 or the buffer solution in the buffer reservoir 30 by movement of the movable stage 26.

This electrophoresis device also includes an electrode 16 whose end portion is inserted into the reservoir 8 of the capillary unit 1, and an electrode 18 arranged so that the end portion thereof is inserted into one of the sample tubes 28 or into the buffer reservoir 30 along with the lower-end portion of the capillary 2.

Figure 6:
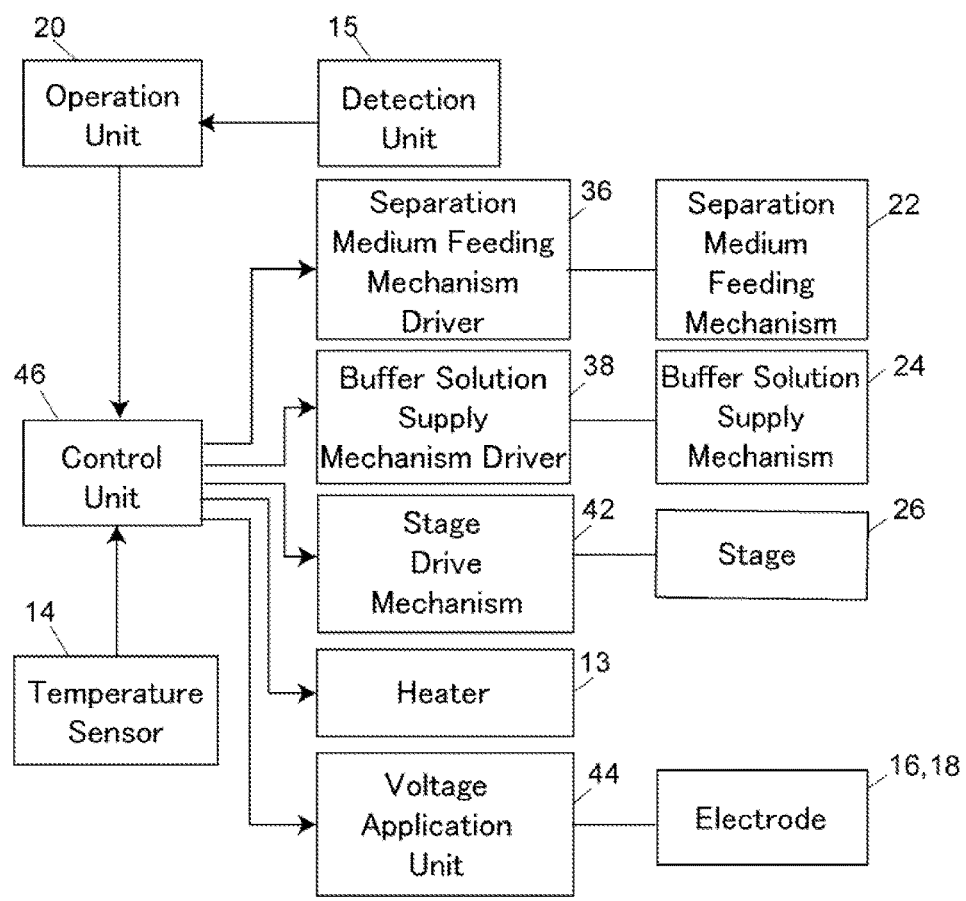
FIG. 6 is a block diagram schematically illustrating a control system of the same embodiment.

A control system of the electrophoresis device of FIG. 4 will be described below using FIG. 6.

Figure 4:
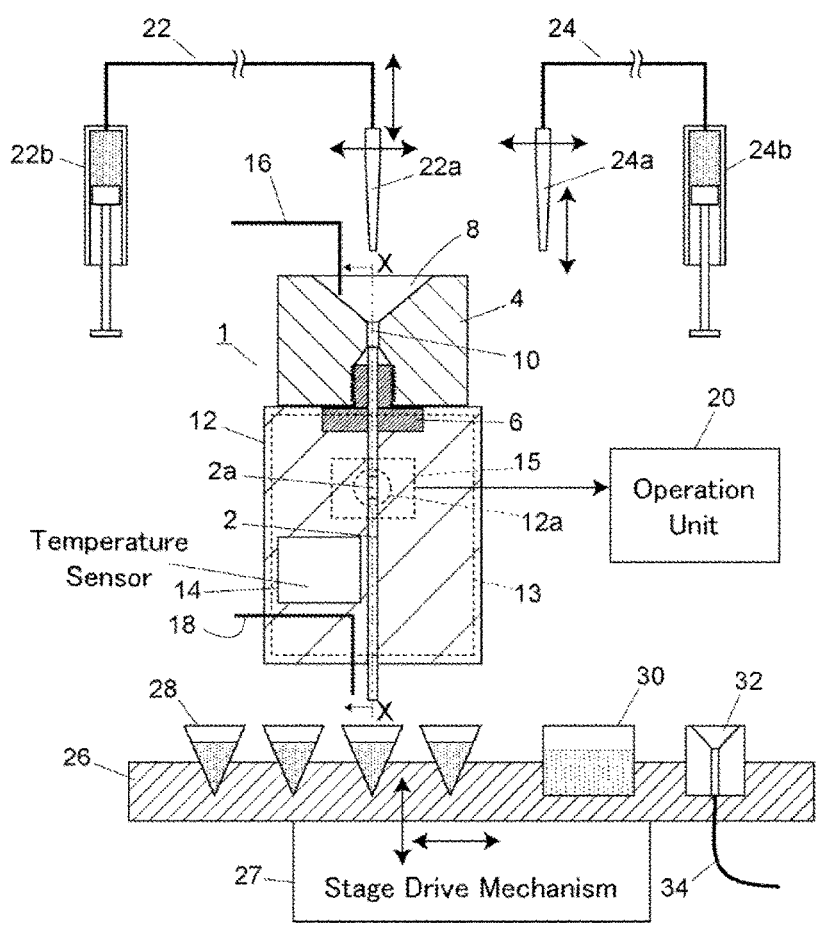
FIG. 4 is a schematic cross-sectional configuration diagram illustrating one embodiment of an electrophoresis device.

Although omitted in FIG. 4, this electrophoresis device is provided with a separation medium feeding mechanism driver 36 that drives the nozzle 22a and the syringe pump 22b of the separation medium feeding mechanism 22, a buffer solution supply mechanism driver 38 that drives the nozzle 24a and the syringe pump 24b of the buffer solution supply mechanism 24, a stage drive mechanism 42 that drives the movable stage 26, and a voltage application unit 44 that applies a voltage across the electrodes 16 and 18. These components are controlled, along with the heater 3, by a control unit 46.

The analyst inputs information, such as information of the sample and analysis conditions, to the operation unit 20. The operation unit 20 provides information, such as the analysis conditions, to the control unit 46 based on the information input by the analyst. The control unit 46 provides a control signal to the separation medium feeding mechanism driver 36, the buffer solution supply mechanism driver 38, the stage drive mechanism 42, and the voltage application unit 44 based on the information provided by the operation unit 20 to control the operation. In addition, the control unit 46 receives a detection signal from the temperature sensor 14 provided in the capillary-unit placement unit 12, and controls an output of the heater 13 so that the temperature of the capillary 2 is maintained at a constant temperature. Furthermore, the operation unit 20 receives a detection signal obtained in the detection unit 15, and the operation unit 20 thus identifies a component of the sample based on detection of an absorbance change in the capillary a or on detection of fluorescence from the inside of the capillary 2.

Figure 7:
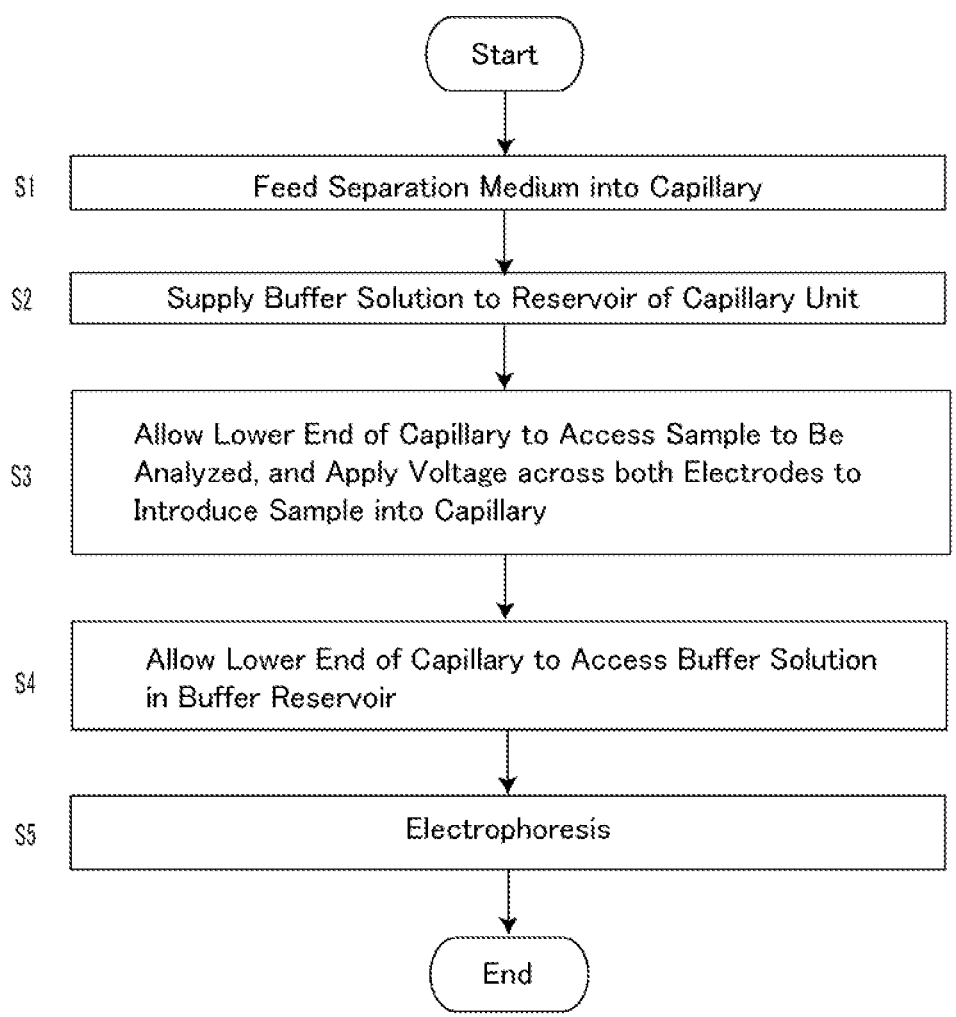
FIG. 7 is a flowchart illustrating one example operation of the same embodiment.

An example of the operation of the embodiment described above will be described below using FIGS. 1 and 7.

The lower end of the capillary 2 is positioned below the drain port 32 by moving the movable stage 26. The nozzle 22a is connected to the nozzle connector 10 of the capillary unit 1 with the polymer suctioned in the syringe pump 22b. The syringe pump 22b is driven to discharge the polymer from the tip of the nozzle 22a, thereby to feed the polymer into the capillary 2 (Step S1).

The polymer to be fed into the capillary 2 may be prepared in such a way that the syringe pump 22b preliminarily suctions a large amount of the polymer, or may be prepared in such a way that the syringe pump 22b which has suctioned a certain amount of water suctions the polymer from a container that contains the polymer during the feed operation of the separation medium to the capillary 2. If the polymer is suctioned by the syringe pump 22b that has suctioned a certain amount of water, suction of air before suction of the polymer, followed by forming an air gap between the water and the air, can prevent the water and the polymer from being mixed together.

After the polymer has been fed into the capillary 2, the nozzle 22a is moved to a position different from that of the reservoir 8, and the nozzle 24a of the buffer solution supply mechanism 24 is moved to a position above the reservoir 8 with the buffer solution suctioned in the syringe pump 24b. The syringe pump 24b is driven to discharge the buffer solution from the tip of the nozzle 24a, thereby to feed the buffer solution to the reservoir 8 (Step S2). An end portion of the electrode 16 is positioned inside the reservoir 8 in advance. Thus, filling the reservoir 8 with the buffer solution causes the end portion of the electrode 16 to be inserted into the buffer solution.

The buffer solution may be supplied to the reservoir 8 in such a way that a large amount of the buffer solution preliminarily suctioned in the syringe pump 24 is discharged from the nozzle 24a, or such that the buffer solution in the buffer reservoir 30 is suctioned using the nozzle 24a on an as-needed basis.

The movable stage 26 is moved so as to position a sample tube 28 containing the sample to be analyzed under the lower end of the capillary 2 and allow the lower end of the capillary 2 to access the sample to be analyzed, at which time the electrode 18 is also inserted into the sample to be analyzed along with the lower end of the capillary 2. A predetermined voltage is applied across the electrodes 16 and 18 to introduce the sample into the capillary 2 by electrical action (Step S3).

Thereafter, the movable stage 26 is moved so as to position the buffer reservoir 30 under the lower end of the capillary 2, and allow the lower end of the capillary 2 to access the buffer solution (Step S4), at which time the electrode 18 is also inserted into the buffer solution along with the lower end of the capillary 2. A predetermined voltage is applied across the electrodes 16 and 18 to perform electrophoresis of the sample (Step S5). Components having different molecular weights contained in the sample have different electrophoretic velocities, and thus, the components pass through the detection position 2a in order of increasing molecular weight.

Figure 8:
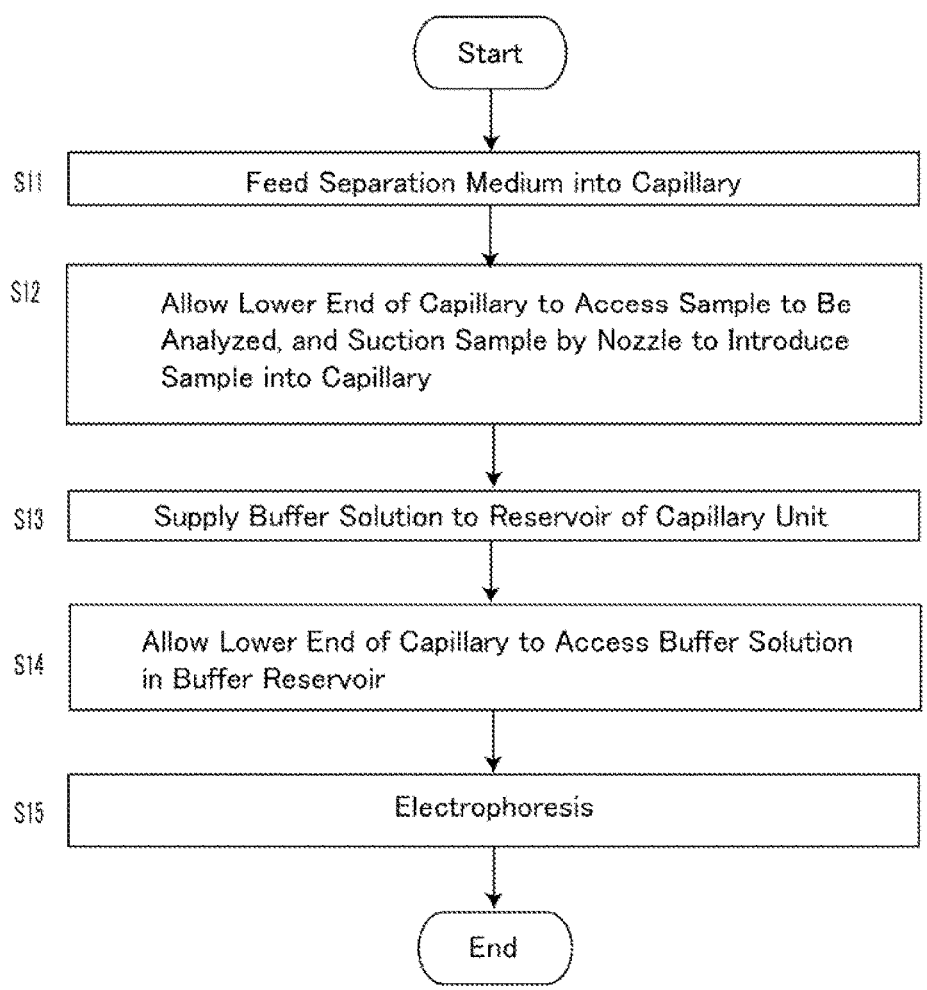
FIG. 8 is a flowchart illustrating another example operation of the same embodiment.

Although the operation described above introduces the sample into the capillary 2 by electrical action, the sample may be introduced into the capillary 2 using the separation medium feeding mechanism 22. FIG. 8 is a flowchart illustrating an example of the operation when the sample is introduced into the capillary 2 using the separation medium feeding mechanism 22. In this operation, the process of introducing the separation medium into the capillary 2 is the same as that of the operation described using FIG. 7.

After the separation medium has been fed into the capillary 2 (Step S1), the movable stage 26 is moved while maintaining the connection of the nozzle 22a to the nozzle connector 10 so as to allow the lower end of the capillary 2 to access the sample to be analyzed, and the syringe pump 22b is driven to suction a predetermined amount of the sample. This operation causes the predetermined amount of the sample to be introduced to a lower-end portion of the capillary 2 (Step S12).

After this, the nozzle 22a is moved to a position different from that of the reservoir 8, and the nozzle 24a of the buffer solution supply mechanism 24 is moved to a position above the reservoir 8 with the buffer solution suctioned in the syringe pump 24b. Then, the buffer solution is discharged from the tip of the nozzle 24a to supply the reservoir 8 with the buffer solution (Step S13). The movable stage 26 is moved so as to position the buffer reservoir 30 under the lower end of the capillary 2, and allow the lower end of the capillary 2 to access the buffer solution (Step S14). Then, a predetermined voltage is applied across the electrodes 16 and 18 to perform electrophoresis of the sample (Step S15).

Figure 9:
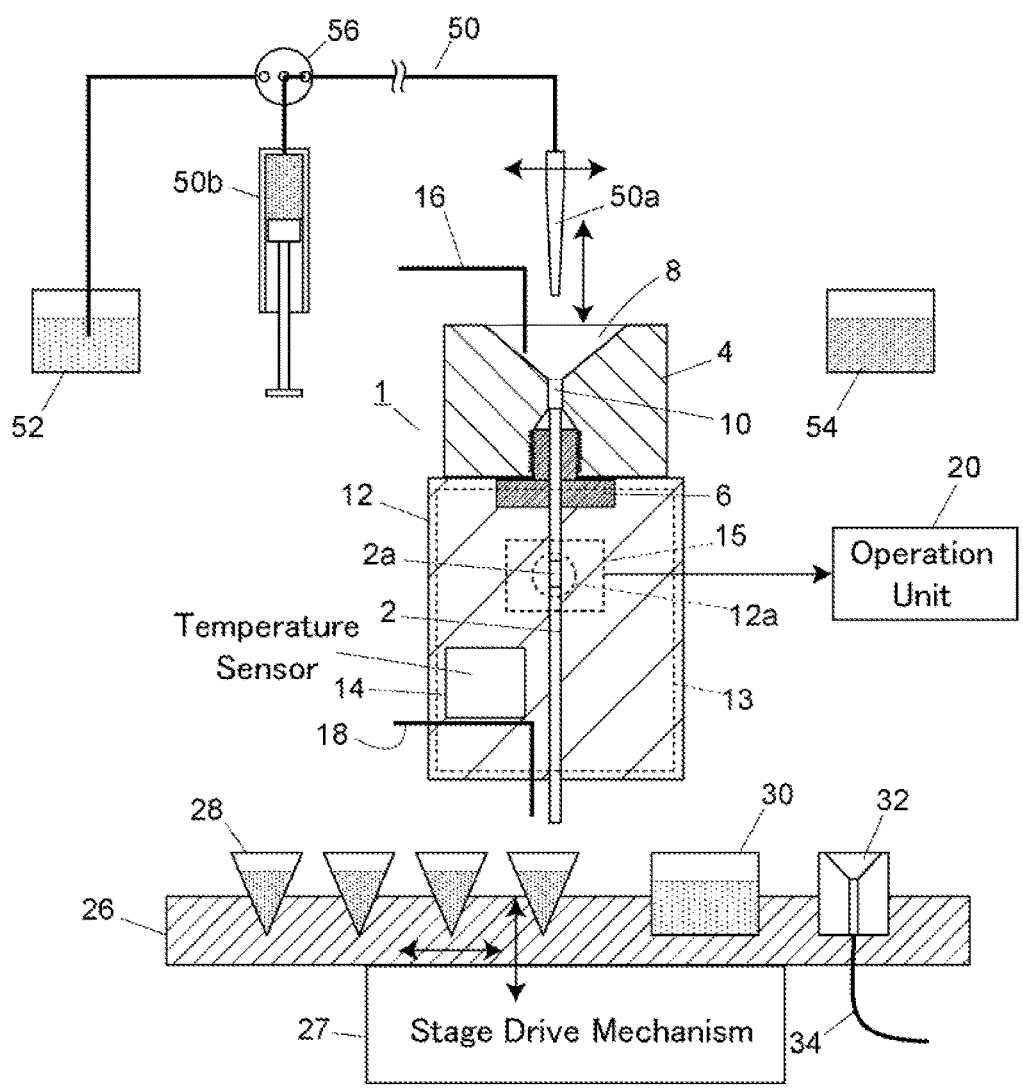
FIG. 9 is a schematic cross-sectional configuration diagram illustrating another embodiment of the electrophoresis device.

FIG. 9 illustrates another embodiment of the electrophoresis device. This embodiment implements the separation medium feeding mechanism 22 and the buffer solution supply mechanism 24 of FIG. 4 by a liquid suction/discharge mechanism 50 of a combined type. The liquid suction/discharge mechanism 50 includes a nozzle 50a that is movable horizontally and vertically, and a syringe pump 50b. A separation medium container 54 containing the separation medium is disposed at a position to which the nozzle 36a can move. The syringe pump 50b is connected to both the nozzle 50a and a cleaning liquid container 52 via a selector valve 56.

Both the separation medium and the buffer solution are suctioned by the nozzle 50a and the syringe pump 50b, and are respectively fed into the capillary 2 and to the reservoir 8. Moreover, the inside of the flow channel of the liquid suction discharge mechanism 50 can be washed as needed.

DESCRIPTION OF REFERENCE SIGNS 1, 1a, 1b: Capillary unit
2: Capillary
2a: Detection position
4, 4a, 4b: Reservoir block
6: Ferrule
8, 9: Reservoir
10: Nozzle connector
12, 12-1, 12-2: Capillary-unit placement unit
12a, 13a: Detection hole
13: Heater
14: Temperature sensor
15: Detection unit
16, Electrode
20: Operation unit
22: Separation medium feeding mechanism
22a, 24a, 50a: Nozzle
22b, 24b, 50b: Syringe pump
24: Buffer solution supply mechanism
26: Movable stage
27: Stage drive mechanism
28: Sample tube
30: Buffer reservoir
32: Drain port
34: Drain tube
36: Separation medium feeding mechanism driver
38: Buffer solution supply mechanism driver
42: Stage drive mechanism
44: Voltage application unit
46: Control unit
50: Liquid suction/discharge mechanism
52: Cleaning liquid container
54: Separation medium container
56: Selector valve

What is claimed is:

1. A capillary unit comprising:
a reservoir having an opening on a top, and formed of a concave portion for retaining a liquid;
a capillary for electrophoresis having a linear shape and extending in a direction away from the opening of the reservoir, one end of the capillary being secured on a bottom-end portion of the reservoir; and
a nozzle connector provided between a bottom of the reservoir and the one end of the capillary, the nozzle connector being configured to provide liquid-tight removable connection with a nozzle inserted into the reservoir through the opening for injecting a liquid into the capillary from the reservoir.

2. The capillary unit according to claim 1, wherein
multiple ones of the capillary, and multiple ones of the reservoir respectively associated with the multiple ones of the capillary, are provided, and
the multiple ones of the reservoir are integrated with one another.

3. The capillary unit according to claim 1, wherein
multiple ones of the capillary are provided, and
the multiple ones of the capillary are connected to a common reservoir respectively through each of multiple ones of the nozzle connector.

4. An electrophoresis device comprising:
a capillary-unit placement unit for placing a capillary unit, the capillary unit comprising a reservoir formed of a concave portion capable of retaining a liquid, a capillary having a linear shape and extending in a direction away from an opening of the reservoir, one end of the capillary being secured on a bottom-end portion of the reservoir; and a nozzle connector provided between a bottom of the reservoir and the one end of the capillary, the nozzle connector being configured to provide liquid-tight removable connection with a nozzle for injecting a liquid into the capillary from the reservoir, the capillary-unit placement unit being configured to place the capillary unit so that the capillary is in a vertical position;
a separation medium feeding mechanism having a nozzle that discharges a separation medium from a tip, and configured to connect the nozzle to the nozzle connector of the capillary unit placed in the capillary-unit placement unit to feed the separation medium into the capillary;
a buffer solution supply mechanism configured to supply a buffer solution to a reservoir of the capillary unit;
a sample holder configured to hold a sample in the sample holder, having an open top to allow a lower end of the capillary to contact with the sample, and to be positioned below the capillary-unit placement unit when the lower end of the capillary comes into contact with the sample;
a buffer reservoir configured to hold the buffer solution in the buffer reservoir, having an open top to allow the lower end of the capillary to contact with the buffer solution, and to be positioned below the capillary-unit placement unit when the lower end of the capillary comes into contact with the buffer solution;
electrodes for applying a voltage across both ends of the capillary; and
a detector configured to optically detect the sample that migrates in the capillary.

5. The electrophoresis device according to claim 4, wherein
the capillary-unit placement unit includes a thermally conductive block that holds a portion other than a lower-end portion of the capillary, and a heater that heats the block.

6. The electrophoresis device according to claim 5, wherein
the heater is a rubber heater attached over an entire surface of the block.

7. The electrophoresis device according to claim 4, wherein
the sample holder and the buffer reservoir are provided on a movable stage that moves along a direction in a horizontal plane and along a vertical direction, so that movement of the stage causes the lower end of the capillary to contact with the sample in the sample holder and the lower end of the capillary to contact with the buffer solution in the buffer reservoir.

8. The electrophoresis device according to claim 4, further comprising:
a control unit configured to control an operation of the electrophoresis device,
wherein
the control unit is configured to introduce the sample into the capillary by applying a voltage across both ends of the capillary with the lower end of the capillary being in contact with the sample in the sample holder after feeding the separation medium into the capillary and then feeding the buffer solution to the reservoir of the capillary unit.

9. The electrophoresis device according to claim 4, further comprising:
a control unit configured to control an operation of the electrophoresis device,
wherein
the control unit is configured to introduce the sample into the capillary by inserting the lower end of the capillary into the sample holder with the nozzle being connected to the nozzle connector and suctioning the separation medium in the capillary using the inlet nozzle after the nozzle is connected to the nozzle connector of the capillary unit and then the separation medium is fed into the capillary.

* * * * *